US011448645B2

(12) United States Patent
Loeffert et al.

(10) Patent No.: US 11,448,645 B2
(45) Date of Patent: Sep. 20, 2022

(54) MICROPARTICLE FOR CULTIVATING AND TESTING CELLS

(71) Applicant: Biomillenia SAS, Romainville (FR)

(72) Inventors: Dirk Loeffert, Haan (DE); Aleksander Dajkovic, Romainville (FR); Thomas Duboys, Romainville (FR)

(73) Assignee: Biomillenia SAS, Romainville (FR)

( * ) Notice: Subject to any disclaimer, the term of this patent is extended or adjusted under 35 U.S.C. 154(b) by 0 days.

(21) Appl. No.: 16/490,804

(22) PCT Filed: Mar. 2, 2018

(86) PCT No.: PCT/EP2018/055220
§ 371 (c)(1),
(2) Date: Sep. 3, 2019

(87) PCT Pub. No.: WO2018/158450
PCT Pub. Date: Sep. 7, 2018

(65) Prior Publication Data
US 2020/0003770 A1 Jan. 2, 2020

(30) Foreign Application Priority Data
Mar. 3, 2017 (EP) .................... 17159201

(51) Int. Cl.
*G01N 33/543* (2006.01)
*C12N 5/071* (2010.01)
*C12Q 1/02* (2006.01)

(52) U.S. Cl.
CPC ..... *G01N 33/54306* (2013.01); *C12N 5/0679* (2013.01); *C12Q 1/02* (2013.01); *C12N 2502/70* (2013.01)

(58) Field of Classification Search
CPC .................................................. C12N 5/0679
See application file for complete search history.

(56) References Cited

U.S. PATENT DOCUMENTS

| 2012/0003285 A1 | 1/2012 | Bibette et al. |
| 2013/0203161 A1 | 8/2013 | Marzorati et al. |
| 2013/0230859 A1 | 9/2013 | Wacklin et al. |
| 2016/0333310 A1 | 11/2016 | Giarratana et al. |

FOREIGN PATENT DOCUMENTS

| WO | 32060276 | 8/2002 |
| WO | 2008116319 | 10/2008 |
| WO | 2009015390 | 1/2009 |
| WO | 2011075848 | 6/2011 |

OTHER PUBLICATIONS

Strand et al., "Alginate-polylysine-alginate microcapsules: effect of size reduction on capsule properties", Journal of Microencapsulation, 2002, 19(5), pp. 615-630.
Strand et al., "Alginate as immobilization matrix for cells", Minerva Biotecnologica, 2000, 12, pp. 223-233.

*Primary Examiner* — Bin Shen
(74) *Attorney, Agent, or Firm* — Stradley Ronon Stevens & Young, LLP

(57) ABSTRACT

Cultivation and/or test-system comprising at least two cultivation spaces combined in a microparticle, wherein the sperically shaped microparticle comprises, (i) a first cultivation space in the center core of said spherically shaped microparticle, (ii) a second cultivation space in the wall surrounding the core of said microparticle, (iii) wherein the wall surrounding the core allows for the exchange of molecules as, salts, nutrients, peptides, chemicals and other compounds in order for the cells in the first cultivation space to interact with the cells in second cultivation space and vice versa. In the test system, the cells are co-cultivated and the microparticles are then selected based on the phenotype of the cells in the first or second cultivation space.

13 Claims, 2 Drawing Sheets

Specification includes a Sequence Listing.

MICROPARTICLE FOR CULTIVATING AND TESTING CELLS

FIELD OF THE INVENTION

The invention is in the field of cellular, in particular strain development. It relates to the selection of bacterial cells after undergoing co-cultivation in the presence of eukaryotic cells or specific bacterial strains. The present application is in the field of cell culture analysis. More precisely in the field of cell culture analysis on single or multi-cell level. The application is also in the field of microfluidics and/or FACS analysis of cells by means of phenotypic sorting.

BACKGROUND

Microbiomes inhabit all ecological niches in very diverse and extreme environments, including microbiomes living in symbiosis with other living organisms. These microbiomes can be affected by external factors such as, but not limited to the intake of antibiotics, the type of nutrition, or the overwhelming growth of microbial pathogens that can lead to so-called dysbiosis. Dysbiosis (also called dysbacteriosis) is a term for a microbial imbalance or maladaptation on or inside the body such as an impaired microbiota. For example, a part of the human microbiota, such as the skin flora, gut flora, or vaginal flora, can become deranged, with normally dominating species underrepresented and normally outcompeted or contained species increasing to fill the void.

Dysbiosis is most commonly reported as a condition in the gastrointestinal tract, particularly during small intestinal bacterial overgrowth or small intestinal fungal overgrowth. Typical microbial colonies found on or in the body are normally benign or beneficial. These beneficial and appropriately sized microbial colonies carry out a series of helpful and necessary functions, such as aiding in digestion or contributing to protect the body from the penetration of pathogenic microbes. These beneficial microbial colonies compete with each other for space and resources and outnumber human cells by a factor 10:1.

A large number of scientific studies have reported among others the beneficial effects, on the health, of certain microorganisms present in the gut or other body environment such as the skin or vagina. Others have been shown to be present in fermented food, in particular dairy products. These microorganisms are commonly referred to as "probiotics" (FAO/WHO report on evaluation of health and nutritional properties of probiotics in food, including powder milk containing live lactic acid bacteria; Cordoba, Argentina; Oct. 1-4, 2001).

Until now, it is inherently difficult to isolate and test the potential beneficial microbes out of the huge diversity of microbes contained in natural samples. Even the testing of the effects of already isolated bacterial strains is difficult, since currently no method exists to study a large number of bacterial strains and their interaction with other bacterial strains, microbiomes or mammalian cells. To date, testing is mostly limited to larger fermentation devices, microtiter plate based testing or smaller e.g. microfluidic devices with chambers that only allow for a limited number of samples to be tested in parallel.

No high-throughput method exists that goes beyond multiple microtiter plates tested in parallel. A more advanced route to higher throughput in culturing microbes can be achieved in droplet-based microfluidics or millifluidics. However, as cells become encapsulated in separate droplets, they cannot stay in physiological contact and therefore cannot be selected based on the result of a physiological interaction between the microbial strain and the selector cell. Inclusion of both, the microbial cell and the selector cell into a single droplet may not promote the desired beneficial effect and rather might stay in competitive conditions and are not able to be supplied with appropriate selection conditions. One particular preferred selection condition might be a close to anaerobic growth environment of microbial cells as e.g. exists in the gut. By inclusion of both mammalian cells that require oxygen and bacterial cells that shall rather grow in anaerobic conditions cannot be promoted when physically being co-located in a droplet.

SUMMARY OF THE INVENTION

The present invention provides an ultrahigh-throughput method that allows the co-culture of microbial strains or other selector cell models such as mammalian cell lines with a high number of microbial strains or even microbiome samples for the testing and/or screening for particular beneficial effects such as, but not limited to probiotic effects, and subsequent isolation of such bacterial strains. The throughput is unprecedented as it is theoretically not limited and can achieve selection of up to $10^9$ microbial strains and higher in parallel.

A first aspect of the invention relates to a cultivation and/or test-system comprising at least two cultivation spaces combined in a microparticle, wherein the spherically shaped microparticle comprises i) a first cultivation space in the center core of said spherically shaped microparticle, ii) a second cultivation space in the wall surrounding the core of said microparticle, wherein the wall surrounding the core allows for the exchange of molecules as, salts, nutrients, peptides, chemicals and other compounds in order for the cells in the first cultivation space to interact with the cells in the second cultivation space and vice versa, and wherein the first cultivation space contains bacterial cells and the second cultivation space contains eukaryotic cells or vice versa.

According to a second aspect, the invention further relates to a method of co-cultivating and/or testing bacterial cells and eukaryotic cells together in a microparticle system as described above, the method comprising the steps of:

i) co-cultivating said bacterial cells and eukaryotic cells in said microparticle system, ii) giving the co-cultivated cells time to interact by means of compound diffusion between the two spaces, iii) sorting said microparticles based on a phenotype of one or more groups of cells present in one or more of the microparticles, wherein the phenotype comprises a probiotic phenotype.

A third aspect of the present invention relates to a cultivation and/or test-system comprising at least two cultivation spaces combined in a microparticle, wherein the spherically shaped microparticle comprises, i) a first cultivation space in the center core of said spherically shaped microparticle, ii) a second cultivation space in the wall surrounding the core of said microparticle, wherein the wall surrounding the core allows for the exchange of molecules as salts, nutrients, peptides chemicals and other compounds in order to allow interaction between the cultivation spaces of said microparticle, wherein the first and/or the second cultivation space contain bacterial cells, eukaryotic cells and/or prebiotic substances.

According to a fourth aspect, the present invention also relates to a cultivation and/or test-system comprising at least two cultivation spaces combined in a microparticle, wherein the spherically shaped microparticle comprises
  i) a first cultivation space in the center core of said spherically shaped microparticle,
  ii) a second cultivation space in the wall surrounding the core of said microparticle,
wherein the wall surrounding the core allows for the exchange of molecules as, salts, nutrients, peptides, chemicals and other compounds in order to allow interaction between the cultivation spaces of said microparticle,
wherein the first cultivation space contains bacterial cells and/or eukaryotic cells, and the second cultivation space contains no cells or vice versa.

DETAILED DESCRIPTION OF THE INVENTION

The invention and its different embodiments are disclosed in further details in this section.

A first aspect of the invention disclosed herein is directed to a cultivation and/or test-system comprising at least two cultivation spaces combined in a microparticle, wherein the spherically shaped microparticle comprises,
  i) a first cultivation space in the center core of said spherically shaped microparticle,
  ii) a second cultivation space in the wall surrounding the core of said microparticle,
wherein the wall surrounding the core allows for the exchange of molecules as, salts, nutrients, peptides, chemicals and other compounds in order for the cells in the first cultivation space to interact with the cells in the second cultivation space and vice versa, and
wherein the first cultivation space contains bacterial cells and the second cultivation space contains eukaryotic cells or vice versa.

Various types of cells can be cultivated in the microparticles, such as bacterial cells, eukaryotic cells, virus particles and fungal cells. However, the present invention relates to the co-cultivation of bacterial cells and eukaryotic cells or the co-cultivation of bacterial cells with other specific bacterial strains. The invention is highly versatile in terms of its use since it finds application in testing antimicrobials specific for a target bacterial pathogen as well as detecting a bacterial strain that could work in synergy with the test strain to obtain a desired outcome.

In a preferred embodiment of the first aspect of the present invention, the bacterial cells in one of the cultivation spaces are colon bacteria and the eukaryotic cells in one of the further cultivation spaces are epithelial colon cells.

Co-cultivation of microbial strains typically present in the gut such as colon bacteria and epithelial colon cells in the system according to the invention, are particularly preferred systems because the inventors have surprisingly found that this can be used as artificial gut system allowing screening or testing for effects of specific colon bacteria strains on epithelial colon cells. Thereby, effects such as probiotic effects of the colon bacteria can be identified.

In the context of the present invention, at least two cultivation spaces are combined in a defined space represented by the microparticle mimicking the natural gut microenvironment. As used herein, the term "combined" refers to the spatial organization of the individual cultivation spaces within a microparticle.

According to the first aspect of the present invention, a first cultivation space is located in the center core of the spherically shaped microparticle. A second (or further) cultivation space(s) surrounds the first cultivation space. The two or more cultivation spaces within the microparticle may mutually interact by means of a wall made of biocompatible porous polymeric matrix, thereby allowing for the exchange of molecules. In the context of the present invention, there is a mutual interaction between different cultivation spaces. This refers to the capability of at least two cultivation space(s) to communicate by exchanging compounds suitable for the growth of the cells. Therefore, the wall is only intended to spatially define the cultivation space(s) within the microparticle.

In the context of the present invention, the molecules exchanged between cells are intended those that allow cells to communicate and respond to the environment.

The exchange occurs through a separation wall that allows the passage of compounds selected from the group comprising amino acids, peptides, carbohydrates, vitamins and minerals.

The microparticle comprising the cultivation spaces is spherically shaped. As used herein, the term "spherical shaped" may refer to microparticle with spherical, oval forms or the like of the microparticle. In the context of the present invention, a spherical form is preferred since it may be advantageous for at least two reasons: i) it may favor the distribution of the second (or further) cultivated space(s) uniformly and homogeneously around the first cultivation space; ii) it maximizes the probability of selecting correctly the microbial strains of interest since they are concentrated in a defined compartment (cultivation space) of the microparticle.

In one embodiment of the invention, the method of co-cultivating and/or testing bacterial cells and eukaryotic cells together in a microparticle system as described above is used to co-cultivate and/or test colon bacteria and epithelial colon cells.

According to a second aspect, the present invention further relates to a method of co-cultivating and/or testing bacterial cells and eukaryotic cells together in a microparticle system as described above, the method comprising the steps of
  i) co-cultivating said bacterial and eukaryotic cells in said microparticle system,
  ii) giving the co-cultivated cells time to interact by means of compound diffusion between the two spaces,
  iii) sorting said microparticles based on a phenotype of one or more groups of cells present in one or more of the microparticles, wherein the phenotype comprises a probiotic phenotype.

As used herein, the term "microparticle system" refers to microparticle according to the first aspect of the present invention comprising one or more cultivation spaces.

The time of co-cultivation step (ii) can vary according to the growth response of a bacterial strain as well as the production of the compound of interest to be detected. In the context of the present invention, co-cultivation time ranges from 15 min up to several days.

In one embodiment of the invention, the method of co-cultivating and/or testing bacterial cells and eukaryotic cells together in a microparticle system as described above is used to co-cultivate and/or test colon bacteria and epithelial colon cells.

As used herein, the term "probiotic phenotype" refers to an expressed trait from a first microorganism providing beneficial effects to a second microorganism. In the context of the present invention the terms "probiotic phenotype" and "probiotic effect" can be used interchangeably.

In one embodiment of the present invention, the probiotic phenotype of the one or more groups of cells is determined by detection of probiotic effects of the bacterial cells on the co-cultivated eukaryotic cells or vice versa.

According to another embodiment, the probiotic effects are selected from the group comprising antimicrobial effects, antifungal effects, promotion of growth, immunomodulatory effects and neurological modulatory effects. The probiotic effects may also refer to modulatory effects, which improve conditions of dysbiosis, for example by re-establishing a balanced bacterial population after an overwhelming growth of certain bacterial species, e.g. during dysbiosis.

Dysbiosis is a multifactorial disorder that can be associated with illnesses such as periodontal disease, inflammatory bowel disease, chronic fatigue syndrome, obesity, cancer, bacterial vaginosis and colitis. Dysbiosis is defined as a condition of microflora imbalance in the gastrointestinal tract, particularly due to small intestinal bacterial and/or fungal overgrowth.

According to another embodiment, the microparticles according to the invention can contain prebiotic substances. Prebiotic substances are substances that induce growth or activity of microorganisms such as bacterial cells, and thereby contribute to the well-being of their host. This phenomenon occurs for example in the gastrointestinal tract or the skin, where prebiotics are able to affect the composition of organisms in the gut microbiome or skin microbiome respectively.

Prebiotic substances are substances having prebiotic effects on bacterial and/or eukaryotic cells. In the context of the present invention, prebiotic effects refer to the promotion of growth of bacterial and/or fungal strains, thereby promoting a balanced microbiome. Prebiotic substances are e.g. trans-galactooligosaccharide and inulin. Other dietary fibers also fall within the definition of prebiotics such as larch arabinogalactin, resistant starch, pectin, beta-glucans and xylooligosaccharides, but may also include other molecules such as amino acids, peptides, proteins, nucleotides and lipids.

According to another embodiment, the prebiotic substance is selected from the group comprising oligosaccharides, polysaccharides, fibers trans-galactooligosaccharide, inulin or any other substance having prebiotic effects on bacterial and/or eukaryotic cells.

In one embodiment of the invention, the bacterial cells in the microparticles are selected by their phenotypic reaction to the presence of prebiotic substances contained in the second of further cultivation spaces within the microparticle or vice versa. In another embodiment, bacterial cells may produce or be the source of prebiotic substances.

In a further embodiment, the bacterial cells may show phenotypic plasticity. In the context of the present invention, the term "phenotypic plasticity" refers to the ability of an organism to change its phenotype in response to changes in the environment. Phenotypic plasticity may or may not be permanent and it encompasses morphological and/or physiological changes.

The herein disclosed method is also suitable for the analysis of probiotic effects of at least one or multiple bacterial strains on another bacterial strain as it exists in nature.

According to another embodiment of the present invention, the probiotic effects of at least one or multiple bacterial strains isolated from natural samples comprising, but not limited to, feces microbiome samples, gut microbiome samples, vaginal microbiome samples, soil microbiome samples and skin microbiome samples on eukaryotic cells such as, but not limited to, mammalian cells, are analyzed.

According to another embodiment, the probiotic effects of the co-cultivated cells in one microparticle is determined by means of cell proliferation assays, immunomodulatory assays, assays to measure cytokines, interleukins, leukotrienes, hormones, histamine, nitric oxide, neurotransmitters.

According to one embodiment, the probiotic effects of the co-cultivated cells in one microparticle can also be accomplished by detection of specific substances such as, but not limited to, cytokines, interleukins, leukotrienes, hormones, histamine, nitric oxide, neurotransmitters, muropeptides, oligosaccharides, teichoic acids, lipoteichoic acids, volatile fatty acids, lipoproteins.

In a preferred embodiment of the invention, the probiotic effects of the co-cultivated bacterial cells on the eukaryotic cells, or vice versa, are analyzed. In an even more preferred embodiment, the probiotic effects of the co-cultivated bacterial cells on the eukaryotic cells are analyzed. Most preferably, the probiotic effects of the co-cultivated colon bacteria on epithelial colon cells are analyzed.

In another embodiment of the invention, the probiotic effects of the bacterial cells in one cultivation space on the eukaryotic cells in the second or further cultivation spaces within a microparticle are analyzed.

In one embodiment of the invention, the microparticles wherein bacterial cells with probiotic properties are detected, can be selected and isolated. Selection and isolation achieved during sorting can be performed by an ultra-high-throughput flow system such as, but not limited to, microfluidics, millifluidics and FACS.

The isolation method according to the invention allows sorting of up to $10^9$ cells and at least 100 cells in parallel. This would represent a remarkable advantage in terms of high-throughputability of the present method over the conventional screening methods known in the art.

Furthermore, according to the invention, the first cultivation space contains at least 1,000,000 cells, more preferably 1,000 cells, yet more preferably 100 cells, even more preferably 10 cells, and most preferably no cells. The second cultivation space contains between 0 and 25,000 cells, more preferably 10 cells, yet more preferably 50 cells, even more preferably 500 cells, and most preferably 1,000 cells.

According to another embodiment, to allow interaction between the co-cultivated bacterial and eukaryotic cells in the microparticles, this should be cultivated for at least 12 hours, preferably 24 hours, and even more preferably 72 hours and/or up to two weeks before being sorted.

The microparticles can be cultivated in a common cell cultivating medium such as, but not limited to, DMEM and RPMI. In one embodiment of the invention, the microparticles are cultivated in mixtures selected from the group comprising diluted soil samples, diluted feces and microbial isolates from the vagina, nasopharynx, sinuses, skin or other natural samples.

According to one embodiment, the microparticles according to the invention can include magnetic beads. The presence of magnetic beads in the microparticles simplifies the purification of the microparticles after cultivation in the desired medium.

The microparticle according to the invention is preferably made of an inner aqueous liquid phase and an outer polymer matrix in a gel phase.

Furthermore, in one embodiment of the invention, the microparticle has two cultivation spaces, the second cultivation space has an inner wall towards the core and an outer wall.

According to the invention, the second cultivation space has a sponge-like structure between the inner wall towards the core and the outer wall. In another embodiment, the first cultivation space has a sponge-like structure within the inner wall of the second cultivation space. Furthermore, the walls of the microparticle comprise a material selected from the group of alginate, agarose, polyacrylamide, chitosan and cellulose.

The cultivation spaces of the microparticle according to the invention have specific a diameter, which can be adjusted according to the desired application. In one embodiment of the invention the first cultivation space has a diameter of between 20 µm and 1 cm, more preferably 500 µm, yet more preferably 250 µm, even more preferably 150 µm, and most preferably 20 µm.

The microparticle dimension presents some technical effects as it is inversely associated with the high-throughputability of the method. In particular, the smaller is the diameter of the microparticle the faster is the capability of the method according to the invention in measuring the physiological effects as the concentration of compounds is higher in smaller volumes.

Also, the thickness of the outer wall of the second space is defined. The diameter is between 500 µm and 10 µm, more preferably 250 µm, yet more preferably 200 µm, even more preferably 150 µm, and most preferably 50 µm.

A method for the production of microparticles is disclosed for example in WO 2010/063937 A1.

An alternative embodiment of the invention discloses a cultivation and/or test-system comprising at least two cultivation spaces combined in a microparticle, wherein the spherically shaped microparticle comprises,
  i) a first cultivation space in the center core of said spherically shaped microparticle,
  ii) a second cultivation space in the wall surrounding the core of said microparticle,
  wherein the wall surrounding the core allows for the exchange of molecules as, salts, nutrients, peptides, chemicals and other compounds in order to allow interaction between the cultivation spaces of said microparticle,
    wherein the first and/or the second cultivation space contain bacterial cells, eukaryotic cells and/or prebiotic substances.

An alternative embodiment of the invention discloses cultivation and/or test-system comprising at least two cultivation spaces combined in a microparticle, wherein the spherically shaped microparticle comprises
  i) a first cultivation space in the center core of said spherically shaped microparticle,
  ii) a second cultivation space in the wall surrounding the core of said microparticle,
  wherein the wall surrounding the core allows for the exchange of molecules as, salts, nutrients, peptides, chemicals and other compounds in order to allow interaction between the cultivation spaces of said microparticle,
    wherein the first cultivation space contains bacterial cells and/or eukaryotic cells, and the second cultivation space contains no cells or vice versa.

EXAMPLES

A strain of *Escherichia coli* (e.g. MG1655) is transformed with a plasmid (named here pTrp) containing the trpABCDE operon under the control of a strong constitutive promoter. The *E. coli* strain harboring pTrp is able to overproduce L-tryptophan and secrete the amino acid to its surrounding, hereafter referred to as the "producer" strain.

A strain of *Saccharomyces cervisiae* that is auxotrophic for L-tryptophan and Histidine (e.g. YFL040W) is transformed with a plasmid (named here as pFluor) containing the coding sequence of a fluorescent protein (e.g. GFP, eGFP, mCherry, RFP) under the control of a strong constitutive promoter ($P_{TEF1}$) as well as the gene or gene operon that allows for intracellular production of histidine. Such complementation of the histidine auxotroph allows for positive selection of *S. cervisiae* harbouring the pFluor plasmid. When cultured in the presence of L-tryptophan but in the absence of Histidine, the auxotrophic *Saccharomyces cervisiae* strain harbouring pFluor proliferates and expresses the fluorescent protein intracellularly. The proliferation of this strain can be monitored via fluorescence measurements, namely illuminating the cells with light of a wavelength or range of wavelengths and measuring the amount of light emitted by the cells at a wavelength or range of wavelengths greater than the wavelength(s) used for illumination. This auxotrophic *Saccharomyces cerevisiae* strain will be referred to hereafter as the "detector strain."

The producer strain is inoculated into a minimal medium (e.g., M9 minimal medium with 4 g/L glucose). This culture is grown for 4-8 hours at 37° C. with shaking at 200 rpm, then diluted to an OD600 of 0.02 using the same minimal medium. The detector strain is inoculated into a synthetically defined medium containing L-tryptophan (to allow for cell growth) but missing histidine (to ensure maintenance of the pFluor plasmid). This detector strain culture is grown for 4-8 hours at 30° C. with shaking at 200 rpm. The detector strain culture is then washed with an isotonic buffer and resuspended using a synthetically defined medium missing both L-tryptophan and histidine.

Figure 1:
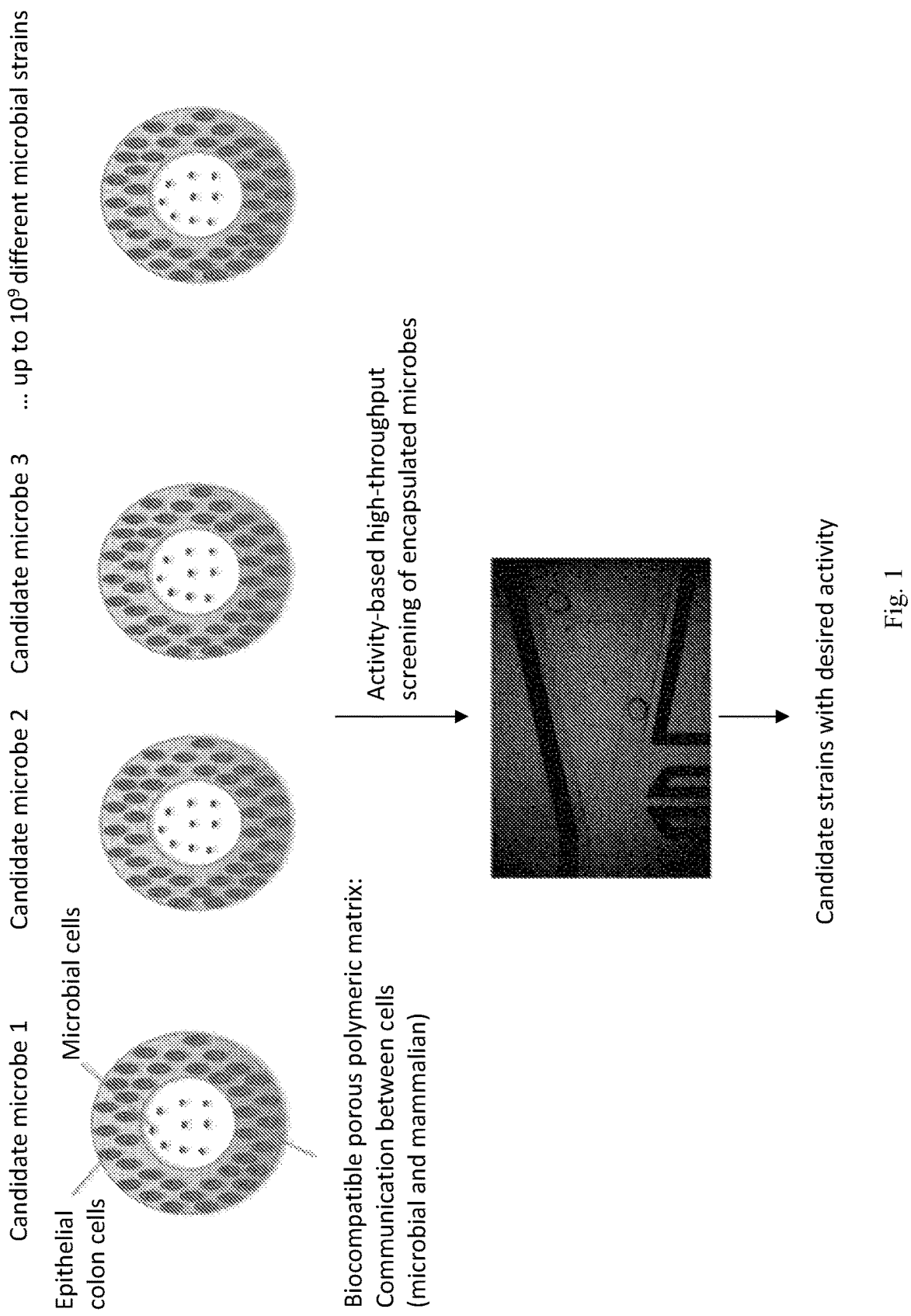
FIG. 1 shows one preferred embodiment of the method according to the invention.
Figure 2:
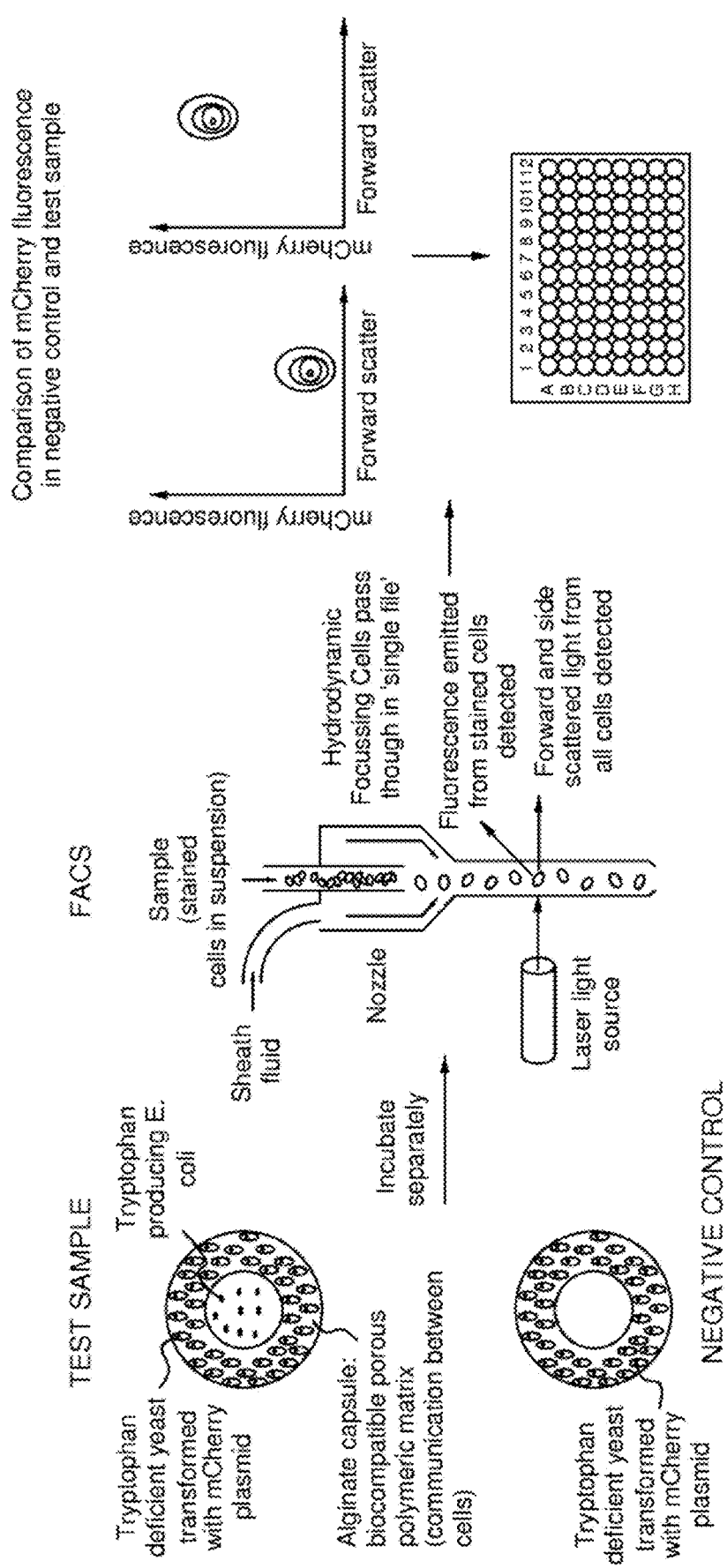
FIG. 2 shows analysis workflow of the method according to the invention.

Alginate core-shell capsules, 30 µm in diameter, are produced using a microfluidic system in which two aqueous solutions, an inner phase containing the producer strain in medium missing histidine and L-tryptophan and an outer phase containing the detector strain in medium missing histidine and L-tryptophan, 2% w/v sodium alginate and 100 mM Ethylenediaminetetraacetic acid calcium disodium salt (hereafter Ca-EDTA), are cut by fluorinated oil (e.g. HFE7500) containing a fluorinated surfactant and 0.15% v/v acetic acid. The acetic acid in fluorinated oil releases the calcium from the EDTA complex. The calcium then binds to the alginate, solidifying it and resulting in a core-shell hydrogel within its core the producer strain and in the hydrogel the detector strain. These capsules are collected and released from the oil shell using perfluoro-1-octanol and resuspended in the same medium missing L-tryptophan as used after washing of the detector strain. Oil is then removed from the solution and the capsules incubated at 30° C. to allow for growth of the producer strain, production of L-tryptophan, subsequent growth of the detector strain, and concomitant production of the fluorescent protein. The capsules are then analyzed and potentially sorted using a FACS (fluorescence activated cell sorting) device, that has the capability of dispensing individual capsules into wells of a microtiter plate. The fluorescence of each capsule is analyzed by illuminating the capsule with a laser having a wavelength corresponding to the excitation maximum of the fluorescent protein of interest and measuring the amount of light emitted by the capsule at a range of wavelengths longer than the wavelength used for illumination/excitation. Capsules exhibiting higher fluorescence must contain higher concentrations of fluorescent protein and must therefore contain a higher number of cells of the detector strain. One may also infer that droplets containing higher numbers of detector strain cells must also contain producer strain cells which generated higher amounts of L-tryptophan. Using the FACS device, capsules exhibiting high levels of fluorescence are separated and/or detected from the remainder of the capsule pool and can be dispensed individually into wells of a microtiter plate as shown in FIG. 2.

Material

Reagents: *Saccharomyces cerevisiae* Meyen ex E. C. Hansen (ATCC® 201168™, atcc), auxotrophic for leucine, histidine and tryptophan; pD1217; pRFSD-mCherry (Biomillenia produced plasmid) (ATUM) Yeast Transformation Kit YEAST1 (Sigma-Aldrich); Yeast Nitrogen Base Without Amino Acids yeast classification medium (Sigma). Yeast synthetic drop-out medium without amino acids (Sigma-Aldrich); Yeast Synthetic Drop-out Medium Supplements without tryptophan (Sigma-Aldrich); Yeast Synthetic Drop-out Medium Supplements without histidine (Sigma-Aldrich); *E. coli* with pSC101-trp.I15 (ATCC); Fluoresceinamine, isomer I (Sigma-Aldrich); N-Hydroxysulfosuccinimide sodium salt (Sigma-Aldrich); MES hemisodium salt (Sigma-Aldrich); N-(3-Dimethylaminopropyl)-N'-ethylcarbodiimide hydrochloride (Sigma-aldrich); SnakeSkin™ Dialysis Tubing, 3.5K MWCO, 22 mm (Thermofisher).

Equipment

Microfluidics

The experimentation is based on the key feature of microfluidic droplet systems that is the use of water-in-oil emulsion droplets to compartmentalize reagents into nanoliter to picoliter volumes. Droplet-based microfluidics manipulate discrete volumes of fluids in immiscible phases with low Reynolds number and laminar flow regimes. Two immiscible phases used for the droplet generation are referred to as the continuous phase (medium in which droplets are generated) and dispersed phase (the droplet phase). The size of the generated droplets is mainly controlled by the flow rates of the continuous phase and dispersed phase, interfacial tension between two phases and the geometry used for the droplet generation. The oil that separates the aqueous phase droplets can prevent cross-contamination between reagents in neighboring droplets and reduce the non-specific binding between channel surface and the reagents. The same technical principles for fluid control and monitoring of droplets using fluorescence microscope were employed.

Preparation of a Microparticle Generating Chip

Soft-lithography in poly(dimethylsiloxane) (PDMS) was used to prepare the microparticle generating device (1). A SU-8 photoresist mould was used to prepare the PDMS. To prepare the SU-8 mold, a layer of SU-8 was spin coated on a silicon wafer. The wafer was covered by a designed mask and exposed to UV for a certain period of time. After full development and baking the wafer, the SU-8 mould was ready for PDMS. The SU-8 thickness for microparticle making chip in this example was 25 µm. The microparticle volume generated by the chip depends on the SU-8 thickness. To generate microparticles, the thickness can vary from 500 µm to 20 µm. After preparation of the SU-8 mould, PDMS was casted on the mould and bound to a glass slide. The inside part of microfluidic channel was treated by a commercial surface coating agent (Trichloro-(1H,1H,2H, 2H-perfluorooctyl)-silane, Sigma-Aldrich) to make the channel surface hydrophobic or layer-by-layer deposition of polyelectrolytes (e.g. Poly(diallydimethylammonium chloride and Poly(sodium 4-strenesulfonate).

Procedure

Staining of Alginate with Fluoresceinamine

For image analysis of the alginate microparticles after production. This will help see if the microparticles are core-shell.

Alginate can be marked fluorescently using the EDC-NHS reaction. Fluorescent molecules can be conjugated with alginate by the binding the amino group of the fluorescent molecule to the carboxylic group of alginates. This reaction is catalyzed by carbodiimides such as 1-ethyl-3-(3-dimethylaminopropyl) carbodiimide (EDC). EDC binds to the carboxylic group to form a very reactive intermediate. The addition of N-Hydroxysulfosuccinimide (Sulfo-NHS) results in an ester Sulfo-NHS intermediate, less susceptible to hydrolysis than its EDC ester precursor. When adding a fluorescent molecule such as fluorescenamine the amine group reacts with the Sulfo-NHS intermediate interchanging the Sulfo-NHS with fluorescenamine to give marked alginate molecules.

Protocol

The labelling of alginate was performed as described in a previous method with modifications (Strand et al. J. Microencapsul. 2002(19):615-630).

The addition of the reagents was performed under mixing with a magnetic stirrer. 2.05 g of alginate were dissolved in 60 mL of distilled water. 50 mL of MES buffer (0.2M MES, pH 5.5) were added to the alginate solution and left overnight. The pH of the MES buffer was adjusted by addition of 1M NaOH or 1M HCl. 0.208 g of EDC and 0.235 g of Sulfo-NHS were dissolved in 3 mL solutions of 9 mM MES buffer and were added successively to the alginate solution. The solution was stirred at room temperature for 30 minutes. 0.188 g of fluorescenamine are then dissolved in 4 mL of 9 mM MES and added to the alginate solution to a concentration of 4.5 mM. The solution was left for the reaction to occur for 18 hours.

Unreacted molecules were removed by dialysis. The alginate solution was added to a 3,500 MWCO dialysis membrane and dialyzed against deionized water with changing of water bi-daily until the water is clear.

The pH of the solution is then adjusted to pH 7.2-7.4 by addition of 1M NaOH or 1M HCl and freeze-dried with protection from light. The dried alginate, labelled with fluorescenamine, is then kept at room temperature and protected from light.

Transformation of *S. cervisae* with red fluorescent protein

Amplification of plasmid with specific mCherry gene sequence and addition of flanking Sapl restriction sites.

For primer: tacacgtacttagtcgctgaagctcttctatgGT-GAGCAAGGGCGAGGAG (SEQ ID NO.1)

Rev primer: taggtacgaactcgattgacggctcttc-taccCTAAAGCTTGTACAGCTCGTC (SEQ ID NO.2)

Uppercase: sequences complementary to extremities of mCherry gene.

Lowercase: sequences for addition of Sapl restriction sites flanking the PCR-product.

Insertion into pD1217

Sapl restriction enzymes, the PCR product, pD1217 and the reaction buffer are combined and incubated at 37° C. for 20 minutes. The plasmid is then transformed into competent *E. coli* and plated on culture plates of LB with kanamycin and incubated overnight at 37° C. A liquid culture complemented with kanamycin and inoculated with the competent cells containing pD1217-mCherry is prepared and the plasmid recovered using a miniprep kit.

Yeast Transformation Protocol

Yeast transformation protocol has been carried out according to the manufacturer's procedure (Sigma-Aldrich) using Yeast Synthetic Drop-out Medium Supplement without histidine for the last step.

Yeast Transformation

For yeast transformation, the following steps have been performed:

1. Prepare YPD and synthetic complete (SC) drop-out medium plates and autoclave them separately.
2. Inoculate yeast cells from plates into 20 ml of YPD medium in a 100 ml sterile flask.
3. Grow overnight with shaking.
4. Dilute cells from above culture into 100 ml of YPD medium until the OD600 is 0.3.
5. Pellet cells gently.
6. Resuspend in 7-8 ml of 1× TE-LiAc solution and rotate at 23° C. for 1-1.5 hours.
7. Add 10 μL of 10 mg/ml salmon testes DNA (Catalog Number D9156, Sigma-Aldrich) in sterile microfuge tubes designated for transformation and one for a negative control.
8. Add 0.1 μg of yeast plasmid DNA (to be studied) to each tube and 1000 of competent cells into each tube and then vortex.

Add marked alginate to 2% w/v to Yeast synthetic drop-out medium supplemeneted with Yeast Synthetic Drop-out Medium Supplements without histidine Inoculate with yeast and check red fluorescence, fluorescence microscope Negative control no inoculation, positive control in YPD with/without alginate Growth of *E. coli*

Growth in Luria-Bertani (LB)

Capsule Making with Trypto Deficient mCherry Producing Yeast and Trypto Producing *E. coli*

1. Culture *E. coli* transformed with pSC101-trp.I15 overnight in yeast Synthetic Drop-out Medium supplemented with yeast Synthetic Drop-out Medium Supplements without L-tryptophan.
2. Culture transformed yeast overnight in yeast Synthetic Drop-out Medium supplemented with yeast Synthetic Drop-out Medium Supplements without histidine, 2% w/v alginate, 100 mM Ca-EDTA.
3. Just before encapsulation the transformed yeast is washed with an isotonic buffer and resuspended in Synthetic Drop-out Medium supplemented with yeast Synthetic Drop-out Medium Supplements without tryptophan.
4. Produce core-shell capsules with yeast in the alginate matrix and *E. coli* in the core and resuspend in yeast Synthetic Drop-out Medium supplemented with yeast Synthetic Drop-out Medium Supplements without Tryptophan.
5. Check mCherry fluorescence during or just after encapsulation and after incubation under fluorescence microscope.

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: Forward primer

<400> SEQUENCE: 1
tacacgtact tagtcgctga agctcttcta tggtgagcaa gggcgaggag          50

<210> SEQ ID NO 2
<211> LENGTH: 53
<212> TYPE: DNA
<213> ORGANISM: Artificial Sequence
<220> FEATURE:
<223> OTHER INFORMATION: Reverse primer

<400> SEQUENCE: 2
taggtacgaa ctcgattgac ggctcttcta ccctaaagct tgtacagctc gtc      53
```

9. Add 600 μL of fresh ly prepared PEG-TE-LiAc solution, vortex, and incubate at 30° C. for 30 minutes with shaking.
10. Optional-DMSO (Catalog Number D8418, Sigma-Aldrich) can be added to 10% (v/v); followed by heat shock for 15 minutes at 42° C.
11. Spin for 3 seconds, resuspend cells in sterile water and plate using appropriate SC drop-out medium.

Growth of *S. cervisae* in Alginate Mixed with Yeast Synthetic Drop-Out Medium Supplemented with Yeast Synthetic Drop-Out Medium Supplements without Histidine

The invention claimed is:

1. A method of co-cultivating and/or testing bacterial cells and mammalian cells together in a microparticle system, the method comprising the steps of:
   i) co-cultivating said bacterial and mammalian cells in said microparticle system,
   ii) giving the co-cultivated cells time to interact by means of compound diffusion between two cultivation spaces,
   iii) sorting up to $10^9$ of said microparticles and at least 100 of said microparticles in parallel based on a phenotype of one or more groups of cells present in one or more of the microparticles.

2. The method according to claim 1, wherein the phenotype of the one or more groups of cells is determined by detection of probiotic effects of the bacterial cells on the co-cultivated mammalian cells wherein the analysis of probiotic effects of the co-cultivated cells in one microparticle is determined by means from the group consisting of cell proliferation assays, immunomodulatory assays and the composition of different bacterial strains.

3. The method according to claim 2, wherein the probiotic effects are selected from the group consisting of antimicrobial effects, antifungal effects, promotion of growth, immunomodulatory effects and neurological modulatory effects.

4. The method according to claim 1, wherein the microparticles contain prebiotic substances.

5. The method according to claim 4, wherein the prebiotic substance is selected from the group consisting of oligosaccharides, polysaccharides, fibers trans-galactooligosaccharide, inulin and any other substance having prebiotic effects on bacterial and/or mammalian cells.

6. The method according to claim 1, wherein the probiotic effects of at least one or multiple bacterial strains isolated from natural samples from the group consisting of feces microbiome samples, gut microbiome samples, vaginal microbiome samples, soil microbiome samples and skin microbiome samples on mammalian cells are analyzed.

7. The method according to claim 4, wherein the analysis of probiotic effects of the co-cultivated cells in one microparticle is determined by detection of specific substances selected from the group comprising cytokines, interleukins, leukotrienes, hormones, histamine, nitric oxide, neurotransmitters, muropeptides, oligosaccharides, teichoic acids, lipoteichoic acids, volatile fatty acids and lipoproteins.

8. The method according to claim 1, wherein the sorting is done by ultrahigh-throughput flow systems from the group consisting of microfluidics, millifluidics and fluorescence activated cell sorting (FACS).

9. The method according to claim 1, wherein a first cultivation space contains at least 1-1.000.000 cells.

10. The method according to claim 1, wherein a second cultivation space contains between 1 and 25.000 cells.

11. The method according to claim 1, wherein the bacterial cells and the mammalian cells in the microparticles are co-cultivated for at least 12 hours and/or up to two weeks before being sorted.

12. The method according to claim 1, wherein the microparticles are cultivated in mixtures selected from the group consisting of diluted soil samples, diluted feces, and microbial isolates from the vagina, nasopharynx, sinuses, skin and other natural samples.

13. The method according to claim 1, wherein the microparticles include magnetic beads.

* * * * *